US010820945B2

(12) United States Patent
Liu et al.

(10) Patent No.: US 10,820,945 B2
(45) Date of Patent: Nov. 3, 2020

(54) SYSTEM FOR FACILITATING MEDICAL TREATMENT

(71) Applicant: CHANG GUNG UNIVERSITY, Taoyuan (TW)

(72) Inventors: Hao-Li Liu, Taoyuan (TW); Shin-Yan Chiou, Zhubei (TW); Chen-Yuan Liao, New Taipei (TW); Wen-Yen Lin, New Taipei (TW); Pin-Yuan Chen, Taoyuan (TW); Kuo-Chen Wei, Taoyuan (TW)

(73) Assignees: CHANG GUNG UNIVERSITY, Taoyuan (TW); CHANG GUNG MEMORIAL HOSPITAL, LINKOU

( * ) Notice: Subject to any disclaimer, the term of this patent is extended or adjusted under 35 U.S.C. 154(b) by 146 days.

(21) Appl. No.: 16/179,020

(22) Filed: Nov. 2, 2018

(65) Prior Publication Data
US 2019/0328462 A1    Oct. 31, 2019

(30) Foreign Application Priority Data
Apr. 30, 2018 (TW) .............................. 107114633 A

(51) Int. Cl.
*A61B 34/20* (2016.01)
*G06T 19/00* (2011.01)
(Continued)

(52) U.S. Cl.
CPC ...... *A61B 34/20* (2016.02); *A61B 17/320068* (2013.01); *A61B 90/37* (2016.02); *G06T 7/70* (2017.01); *G06T 7/80* (2017.01); *G06T 19/006* (2013.01); *G16H 30/20* (2018.01); *G16H 40/63* (2018.01); *A61B 2017/00725* (2013.01); *A61B 2034/105* (2016.02); *A61B 2034/2065* (2016.02); *A61B 2090/365* (2016.02); *A61B 2090/371* (2016.02); *A61B 2090/372* (2016.02);
(Continued)

(58) Field of Classification Search
CPC . A61B 34/20; A61B 90/37; A61B 17/320068; G06T 7/80; G06T 19/006; G16H 30/20; G16H 40/63
See application file for complete search history.

(56) References Cited

U.S. PATENT DOCUMENTS

2013/0267838 A1* 10/2013 Fronk ................... A61B 5/7425
                                                        600/424
2013/0331686 A1* 12/2013 Freysinger ............. A61B 34/20
                                                        600/417
(Continued)

OTHER PUBLICATIONS

Google Scholar Search Results.*

*Primary Examiner* — Qun Shen
(74) *Attorney, Agent, or Firm* — Lewis Roca Rothgerber Christie LLP

(57) ABSTRACT

A system includes an image capturing device, a subject reference marker disposed adjacent to a subject, a tool reference marker disposed on a treatment tool, a display device mounted on an operator, an operator reference marker disposed on the display device, and a processor. The image capturing device includes two image capturing modules that simultaneously and respectively capture two images of the operator, the subject, and the treatment tool. The processor receives the images, analyzes the images to obtain spatial locations of the reference markers, and transmits coordinate information and auxiliary information.

12 Claims, 11 Drawing Sheets

(51) Int. Cl.
*G06T 7/80* (2017.01)
*A61B 90/00* (2016.01)
*A61B 17/32* (2006.01)
*G16H 30/20* (2018.01)
*G16H 40/63* (2018.01)
*G06T 7/70* (2017.01)
*A61B 90/50* (2016.01)
*A61B 17/00* (2006.01)
*A61B 34/10* (2016.01)

(52) U.S. Cl.
CPC ... *A61B 2090/374* (2016.02); *A61B 2090/378* (2016.02); *A61B 2090/3762* (2016.02); *A61B 2090/3983* (2016.02); *A61B 2090/502* (2016.02); *G06T 2207/30201* (2013.01); *G06T 2207/30204* (2013.01); *G06T 2207/30244* (2013.01); *G06T 2210/41* (2013.01)

(56) References Cited

U.S. PATENT DOCUMENTS

| | | | |
|---|---|---|---|
| 2014/0275760 A1* | 9/2014 | Lee | A61B 34/30 600/102 |
| 2016/0191887 A1* | 6/2016 | Casas | H04N 13/279 348/47 |
| 2016/0249989 A1* | 9/2016 | Devam | A61B 5/021 345/633 |
| 2017/0050050 A1* | 2/2017 | Berlinger | G01T 7/005 |
| 2017/0056115 A1* | 3/2017 | Corndorf | G16Z 99/00 |
| 2017/0318235 A1* | 11/2017 | Schneider | G06K 9/00664 |
| 2018/0140362 A1* | 5/2018 | Cal | A61B 34/20 |
| 2019/0311542 A1* | 10/2019 | Douglas | G01S 5/10 |
| 2019/0380798 A1* | 12/2019 | Itkowitz | A61B 1/3132 |

* cited by examiner

SYSTEM FOR FACILITATING MEDICAL TREATMENT

CROSS-REFERENCE TO RELATED APPLICATION

This application claims priority of Taiwanese Invention Patent Application No. 107114633, filed on Apr. 30, 2018.

FIELD

The disclosure relates to a system for facilitating medical treatment, and more particularly to a system for facilitating medical treatment using augmented reality (AR) technology.

BACKGROUND

When performing medical treatment on a patient with a treatment tool, especially for surgical operations, a medical professional is often required to repeatedly switch his/her sight back and forth between the patient and a screen providing surgical assistive information, such as surgical guidance information, causing distraction and inconvenience during treatment.

SUMMARY

Therefore, an object of the disclosure is to provide a system for facilitating medical treatment that can alleviate at least one of the drawbacks of the prior art.

According to one aspect of the disclosure, the system is adapted to be utilized by an operator group to perform an operation on a subject with assistance of a treatment tool. The system includes an image capturing device, a subject reference marker, a tool reference marker, at least one display device, at least one operator reference marker and a processor. The image capturing device includes two image capturing modules that are configured to simultaneously and respectively capture two images of the operator group, the subject, and the treatment tool. The subject reference marker is to be disposed adjacent to the subject. The tool reference marker is to be disposed on the treatment tool. The at least one display device is configured to be mounted on one member of the operator group. The at least one operator reference marker is disposed on said at least one display device. The processor is electrically connected to the image capturing device, and is communicable with said at least one display device. The processor is configured to receive the images, to perform a spatial analysis on the images so as to obtain spatial locations of the subject reference marker, the tool reference marker and the at least one operator reference marker. The processor is configured to transmit auxiliary information regarding the subject and coordinate information regarding the spatial locations to the at least one display device.

According to another aspect of the disclosure, the system for facilitating medical treatment is adapted to be utilized by an operator group to perform an operation on a subject with assistance of a treatment tool. The system includes an image capturing device, a first inertial sensor, a tool reference marker, a second inertial sensor and a processor. The image capturing device is configured to capture an image of the treatment tool. The first inertial sensor is disposed on the image capturing device, and is configured to make inertial measurement of the image capturing device and to generate a first orientation vector based on a result of the inertial measurement of the image capturing device. The tool reference marker is to be disposed on the treatment tool. The second inertial sensor is disposed on the tool reference marker, and is configured to make inertial measurement of the tool reference marker and to generate a second orientation vector based on a result of the inertial measurement of the tool reference marker. The processor is electrically connected to the image capturing device, the first inertial sensor and the second inertial sensor, and is configured to receive the image, the first orientation vector and the second orientation vector, and to calculate coordinates defining a spatial location of the tool reference marker with respect to the image capturing device based on the first orientation vector, the second orientation vector, an area of the tool reference marker in the image, and a position of the tool reference marker in the image.

BRIEF DESCRIPTION OF THE DRAWINGS

Other features and advantages of the disclosure will become apparent in the following detailed description of the embodiments with reference to the accompanying drawings, of which.

DETAILED DESCRIPTION

Figure 1:
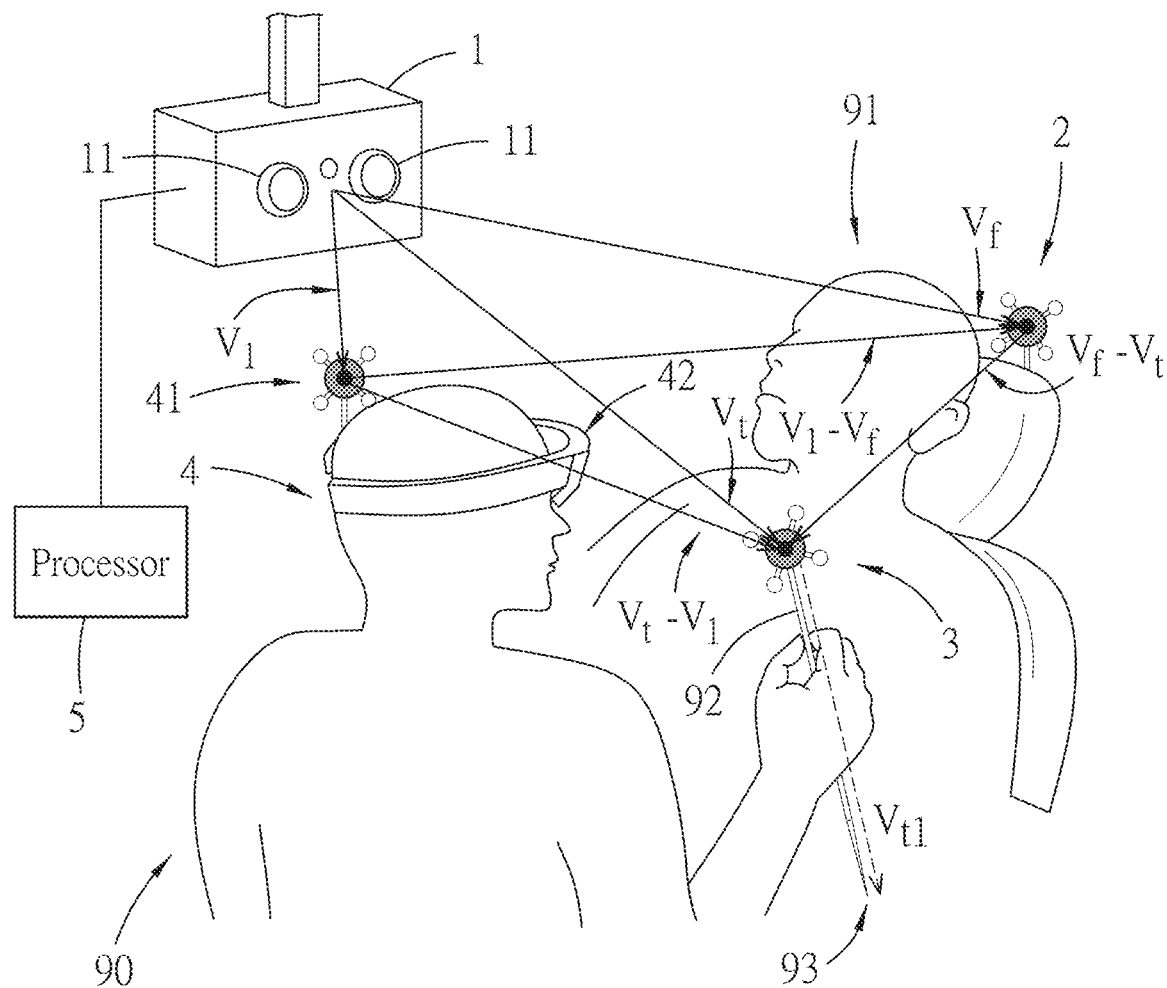
FIG. 1 is a schematic diagram illustrating a first embodiment of a system for facilitating medical treatment according to the disclosure.

Before the disclosure is described in greater detail, it should be noted that where considered appropriate, reference numerals or terminal portions of reference numerals have been repeated among the figures to indicate corresponding or analogous elements, which may optionally have similar characteristics.

Referring to FIG. 1, a first embodiment of a system for facilitating medical treatment is illustrated. The system is adapted to be utilized by an operator group 90 (only one member of the operator group is illustrated) to perform an operation on a subject 91 with assistance of a treatment tool 92. The system includes an image capturing device 1, a subject reference marker 2, a tool reference marker 3, at least one display device 4, at least one operator reference marker 41, and a processor 5.

The image capturing device 1 includes two image capturing modules 11 that are configured to simultaneously and respectively capture two images of the operator group 90, the subject 91 and the treatment tool 92. Each of said two images contains at least one of the subject reference marker 2, the tool reference marker 3 and said at least one operator reference marker 41. In this embodiment, each of the image capturing modules 11 may be implemented to be a camera or a video recorder, but implementation thereof is not limited to the disclosure herein and may vary in other embodiments. In this embodiment, each of the subject reference marker 2, the tool reference marker 3 and said at least one operator reference marker 41 is implemented to be a circle with a cross, like what is shown in FIG. 1, so they can be recognized by the processor 5 with ease in the images captured by the image capturing device 1. However, implementations of the subject reference marker 2, the tool reference marker 3 and said at least one operator reference marker 41 are not limited to the disclosure herein and may vary in other embodiments. For example, each of the subject reference marker 2, the tool reference marker 3 and said at least one operator reference marker 41 may be implemented to be recognizable by color detection, shape detection, or barcode scan (e.g., coded as a linear barcode or a matrix barcode).

The subject reference marker 2 is disposed adjacent to the subject 91. In this embodiment, the subject 91 is a patient who lies on a chair to undergo surgery, and the subject reference marker 2 is disposed on the chair. The tool reference marker 3 is to be disposed on the treatment tool 92 that is used by one member of the operator group 90 for medical treatment. It should be noted that implementation of each of the number of the tool reference marker 3 and the number of the treatment tool 92 is not limited to one, and may be plural number in other embodiments.

Figure 7:
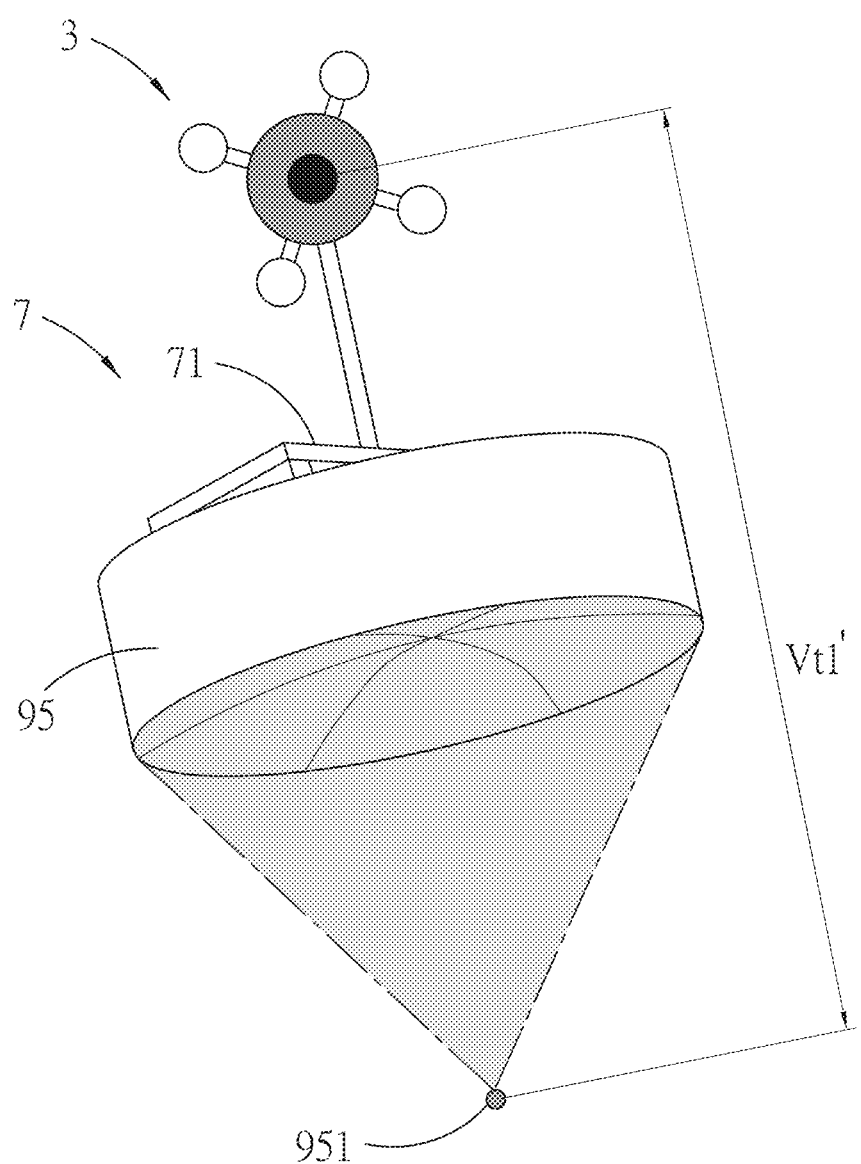
Figure 8:
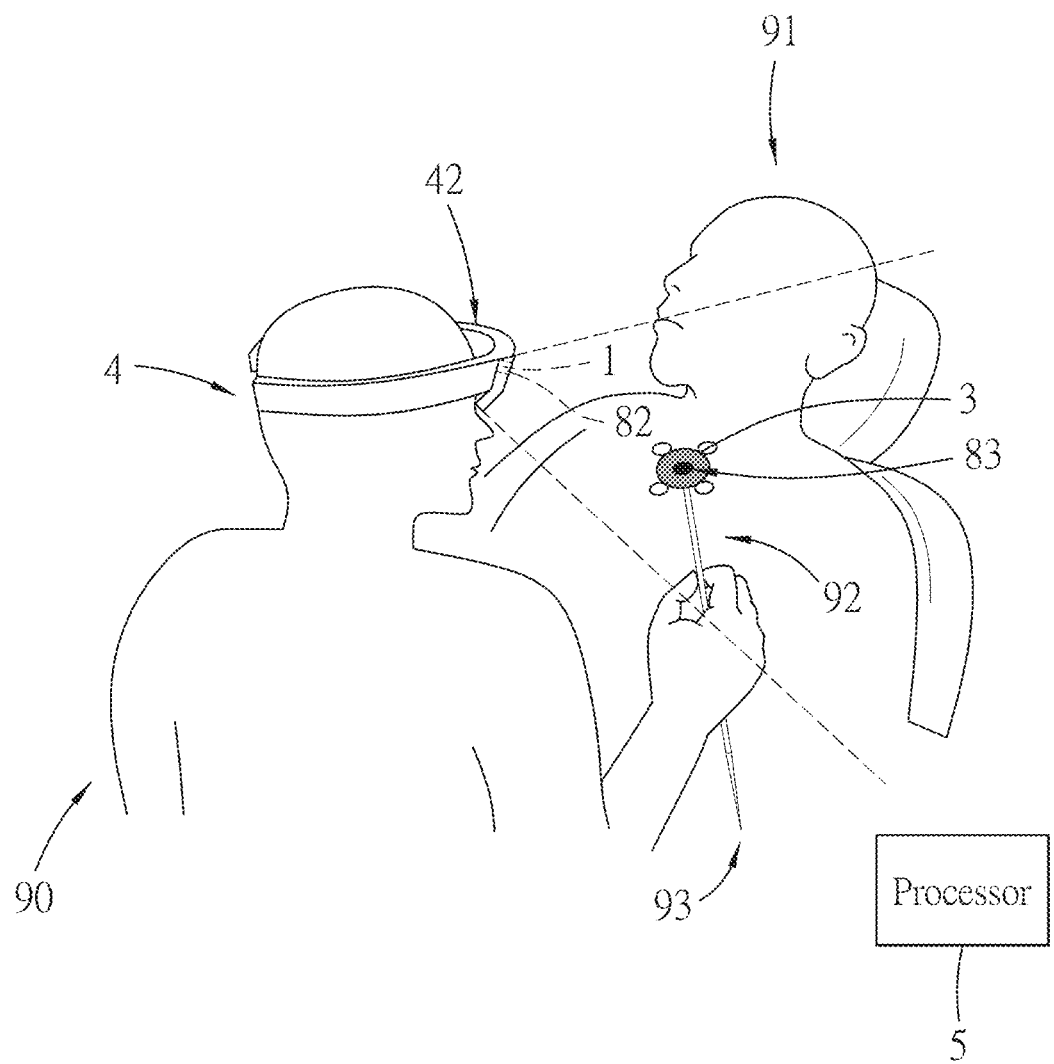
FIG. 8 is a schematic diagram illustrating a second embodiment of the system for facilitating medical treatment according to the disclosure.

Said at least one display device 4 is configured to be mounted on member(s) of the operator group 90. In this embodiment, each of said at least one display device 4 is a head-mounted device including a see-through display 42. Each of said at least one operator reference marker 41 is disposed on a distinct one of said at least one display device 4. For convenience of explanation, the number of said at least one display device 4 is assumed to be one as shown in FIGS. 1 and 8. That is to say, a scenario of a single operator wearing the display device 4 is shown in FIGS. 1 and 7. However, it is worth noting that the number of said at least one display device 4 and the number of member(s) of the operator group 90 are not limited to the disclosure herein and may vary in other embodiments.

The processor 5 is electrically connected to the image capturing device 1, and is communicable with said at least one display device 4 by means of wireless communication. The processor 5 may be implemented by a Central Processing Unit (CPU) in a computer, a microprocessor or any circuit configurable or programmable in a software manner and/or hardware manner to implement functionalities discussed in this disclosure. However, implementation of the processor 5 is not limited to the disclosure herein.

The processor 5 is configured to receive the images, to perform a spatial analysis on the images so as to obtain spatial locations of the subject reference marker 2, the tool reference marker 3 and said at least one operator reference marker 41, and to transmit auxiliary information regarding the subject 91 and coordinate information regarding the spatial locations to said at least one display device 4. It should be noted that implementation of performing the spatial analysis on the images is known to one skilled in the relevant art, so detailed explanation of the same is omitted herein for the sake of brevity, and only a conceptual explanation of the spatial analysis performed by the system according to the disclosure is described as follows, where said at least one operator reference marker 41 and said at least one display device 4 are both assumed to be plural in number.

The processor 5 is configured to calculate coordinate vectors $V=(O, V_1, V_2, \ldots, V_i, \ldots, V_N, V_t, V_f)$ based on the spatial locations of the subject reference marker 2, the tool reference marker 3 and the operator reference markers 41 that are each defined in a form of coordinates in a coordinate system, where O represents coordinates of an origin of the coordinate system and corresponds to a spatial location of the image capturing device 1, N represents a total number of the operator reference markers 41, $V_i$ represents a vector from the origin to coordinates of the $i^{th}$ one of the operator reference markers 41, where i is an integer from one to N, $V_t$ represents a vector from the origin to coordinates of the tool reference marker 3, and $V_f$ represents a vector from the origin to coordinates of the subject reference marker 2.

Additionally, the processor 5 is configured to, based on the coordinate vectors V, calculate a first vector matrix $$X1=(V_t-V_1, V_t-V_2, \ldots, V_t-V_N, V_f-V_t, V_1-V_f, V_2-V_f, \ldots, V_N-V_f)$$

that serves as the coordinate information, in which the spatial location of the image capturing device 1 serves as the origin of the coordinate system. In one embodiment, the processor 5 is configured to transmit the first vector matrix X1 to each of the display devices 4, where $V_t-V_i$ represents a relative vector of the tool reference marker 3 on the treatment tool 92 with respect to the operator reference marker 41 on the $i^{th}$ one of the head-mounted displays 4, $V_f-V_t$ represents a relative vector of the subject reference marker 2 with respect to the tool reference marker 3 on the treatment tool 92, $V_i-V_f$ represents a relative vector of the operator reference marker 41 on the $i^{th}$ one of the head-mounted displays 4 with respect to the subject reference marker 2, where i is an integer from one to N.

Moreover, in one embodiment, the processor 5 is configured to, based on the first vector matrix X1 and a predetermined first spatial transformation matrix T1, calculate a second vector matrix $$X2=T1*X1$$

that serves as the coordinate information, in which the spatial locations of the operator reference markers 41 respectively serve as origins of respective coordinate systems. Subsequently, the processor 5 transmits the coordinate information to the display devices 4 so the display devices 4 obtain plural sets of real-time coordinates of the tool reference marker 3, each with respect to a respective one of the operator reference markers 41. It should be noted that $V_1, V_2, \ldots, V_N$ are obtained in real time. The processor 5 transforms the first vector matrix X1, where the spatial location of the image capturing device 1 serves as the origin, into the second vector matrix X2, where the spatial locations of the operator reference markers 41 respectively serve as origins of respective coordinate systems.

Furthermore, in one embodiment, the processor 5 is configured to, based on the second vector matrix X2 and a predetermined second spatial transformation matrix T2, calculate a third vector matrix $$X3=T2*X3$$

that serves as the coordinate information, in which the spatial locations of the operator reference markers 41 respectively serve as origins of the respective coordinate systems. Then, the processor 5 transmits the coordinate information to the display devices 4 so the display devices 4 obtain plural sets of real-time coordinates of a tip 93 of the treatment tool 92, each with respect to a respective one of the operator reference markers 41. In this embodiment, the tip 93 of the treatment tool 92 is where the treatment tool 92 is to be utilized to contact the subject 91, and a distance (Vt1) between the tip 93 of the treatment tool 92 and the tool reference marker 3 is constant and predetermined. The processor 5 utilizes the predetermined second spatial transformation matrix T2 to transform the second vector matrix X2, which carries the coordinate information regarding the spatial locations of the tool reference marker 3 with respect to the operator reference markers 41 that respectively serve as origins, into the third vector matrix X3, which carries coordinate information regarding the spatial locations of the tip 93 of the treatment tool 92 with respect to the same origins, respectively.

Taking a scenario where the number of the operator reference markers 41 is one (i.e., N=1) as an example, given the first vector matrix $$X1 = \begin{bmatrix} a1 & a2 & a3 & 0 \\ b1 & b2 & b3 & 0 \\ c1 & c2 & c3 & 0 \\ 0 & 0 & 0 & 1 \end{bmatrix},$$

the second vector matrix $$X2 = \begin{bmatrix} d1 & d2 & d3 & 0 \\ e1 & e2 & e3 & 0 \\ f1 & f2 & f3 & 0 \\ 0 & 0 & 0 & 1 \end{bmatrix},$$

and the third vector matrix $$X3 = \begin{bmatrix} g1 & g2 & g3 & 0 \\ h1 & h2 & h3 & 0 \\ i1 & i2 & i3 & 0 \\ 0 & 0 & 0 & 1 \end{bmatrix},$$

the first spatial transformation matrix T1 satisfies a mathematical relationship $$\begin{bmatrix} d1 & d2 & d3 & 0 \\ e1 & e2 & e3 & 0 \\ f1 & f2 & f3 & 0 \\ 0 & 0 & 0 & 1 \end{bmatrix} = T1 * \begin{bmatrix} a1 & a2 & a3 & 0 \\ b1 & b2 & b3 & 0 \\ c1 & c2 & c3 & 0 \\ 0 & 0 & 0 & 1 \end{bmatrix},$$

and can be expressed as $$T1 = \begin{bmatrix} a1 & a2 & a3 & 0 \\ b1 & b2 & b3 & 0 \\ c1 & c2 & c3 & 0 \\ 0 & 0 & 0 & 1 \end{bmatrix} * \begin{bmatrix} d1 & d2 & d3 & 0 \\ e1 & e2 & e3 & 0 \\ f1 & f2 & f3 & 0 \\ 0 & 0 & 0 & 1 \end{bmatrix}^{-1}.$$

Similarly, the second spatial transformation matrix T2 satisfies another mathematical relationship $$\begin{bmatrix} g1 & g2 & g3 & 0 \\ h1 & h2 & h3 & 0 \\ i1 & i2 & i3 & 0 \\ 0 & 0 & 0 & 1 \end{bmatrix} = T2 * \begin{bmatrix} d1 & d2 & d3 & 0 \\ e1 & e2 & e3 & 0 \\ f1 & f2 & f3 & 0 \\ 0 & 0 & 0 & 1 \end{bmatrix},$$

and can be expressed as $$T2 = \begin{bmatrix} d1 & d2 & d3 & 0 \\ e1 & e2 & e3 & 0 \\ f1 & f2 & f3 & 0 \\ 0 & 0 & 0 & 1 \end{bmatrix} * \begin{bmatrix} g1 & g2 & g3 & 0 \\ h1 & h2 & h3 & 0 \\ i1 & i2 & i3 & 0 \\ 0 & 0 & 0 & 1 \end{bmatrix}^{-1}.$$

Figure 2:
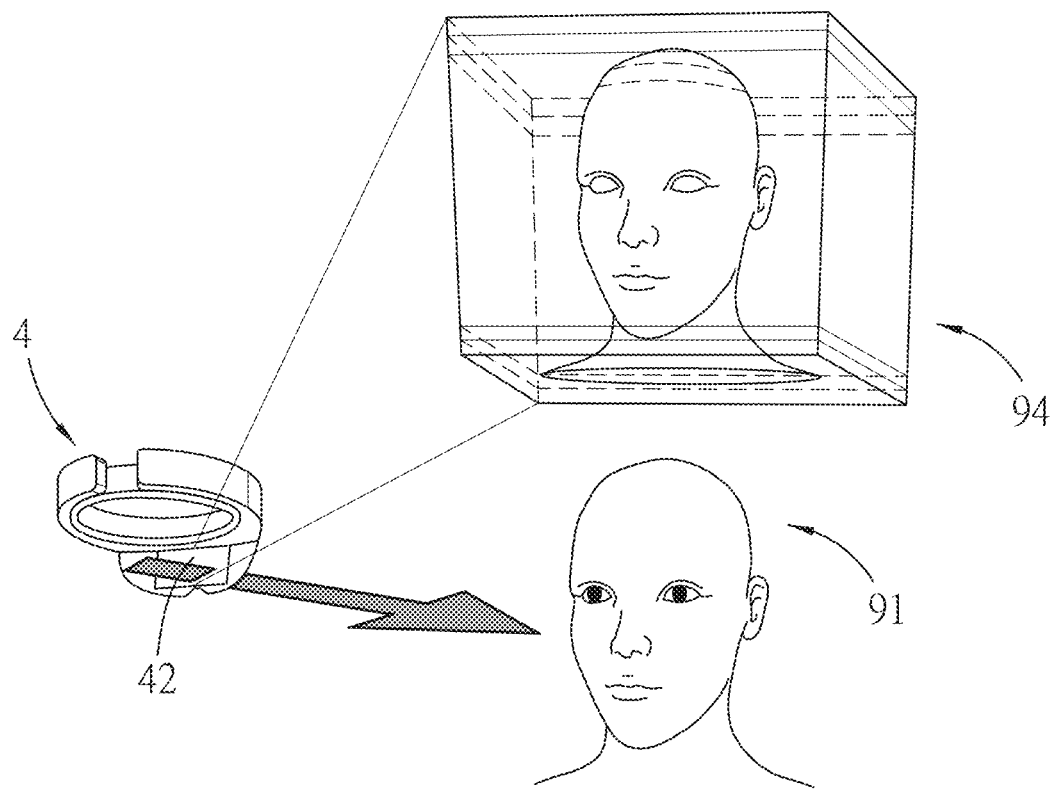
FIG. 2 is a schematic diagram illustrating an embodiment of providing auxiliary information by a display device of the system according to the disclosure.

Further referring to FIG. 2, the auxiliary information contains an augmented reality (AR) object 94 related to treatment of the subject 91. The see-through display 42 of each of said at least one display device 4 is configured to display the AR object 94 at a desired position with respect to one of the subject 91 and the treatment tool 92 based on the auxiliary information and the coordinate information regarding the spatial locations (e.g., the first vector matrix X1, the second vector matrix X2 or the third vector matrix X3) so that the AR object 94 is properly arranged with respect to the subject 91 in space.

The auxiliary information to be displayed on the display device 4 of the system according to the disclosure is illustrated. Through the see-through display 42, a member of the operator group 90 (hereinafter referred to as an operator) who wears the display device 4 is capable of seeing the AR object 94 that is to be fit to a head of the subject 91 (i.e., the patient) in space as what is shown in FIG. 2. Since the AR object 94 is displayed at the desired position where the operator is performing the medical treatment, medical information necessary for the medical treatment may be conveniently perceived. In this way, the operator is able to concentrate on performing the medical treatment and does not have to divert his/her attention elsewhere, thereby facilitating the process of the medical treatment.

In one embodiment, each display device 4 includes a processing module (not shown) that is configured to control the see-through display 42 to display the AR object 94 of the auxiliary information at the desired position with respect to the subject 91 based on the coordinate information regarding the spatial locations (e.g., the first vector matrix X1, the second vector matrix X2 or the third vector matrix X3) received from the processor 5.

In one embodiment, the display device 4 may be replaced by a conventional display such as a liquid-crystal display (LCD) or a light-emitting diode (LED) display that is configured to display the AR object 94 of the auxiliary information.

Figure 3:
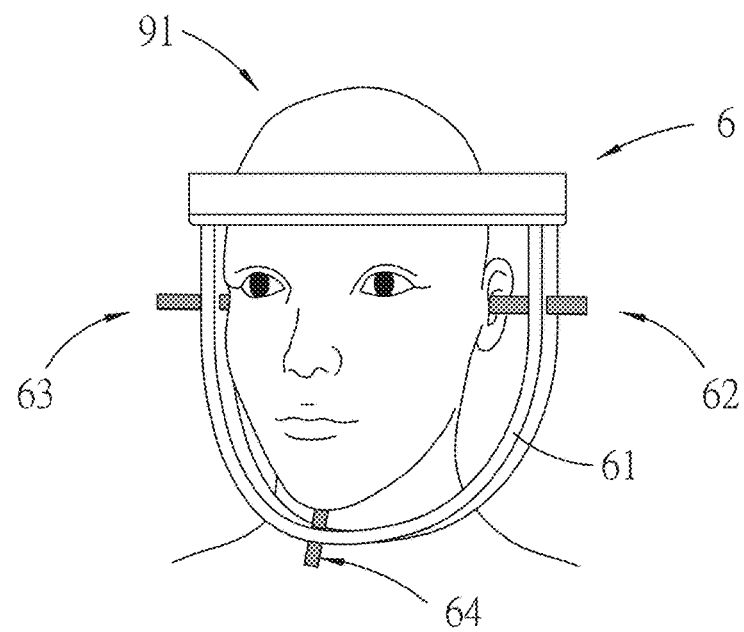
FIG. 3 is a schematic diagram illustrating an embodiment of a positioning frame of the system according to the disclosure.

Referring to FIG. 3, the first embodiment of the system according to the disclosure further includes a positioning frame 6. The positioning frame 6 includes a frame body 61 that is configured to be worn on the head of the subject 91. The positioning frame 6 further includes a first calibration rod 62, a second calibration rod 63 and a third calibration rod 64 that are disposed on the frame body 61. The first calibration rod 62 and the second calibration rod 63 are configured to be arranged along an imaginary axis so that, when the frame body 61 is worn on the head of the subject 91, the first calibration rod 62 and the second calibration rod 63 respectively abut against two ears of the subject 91. The third calibration rod 64 is configured to be arranged to abut against a lower jaw of the subject 91.

Figure 4:
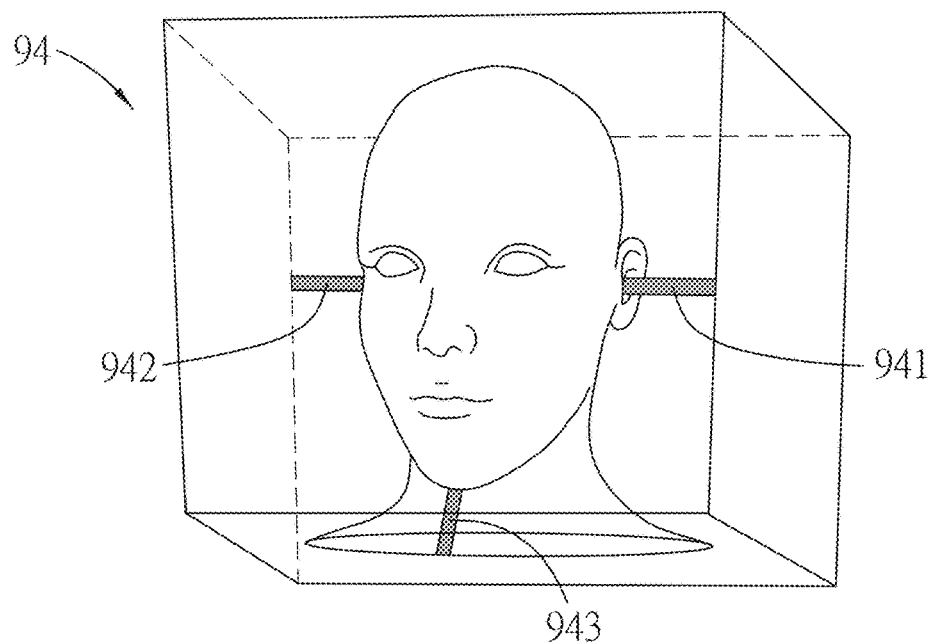
FIG. 4 is a schematic diagram illustrating an embodiment of an augmented reality (AR) object including three virtual calibration rods according to the disclosure.

Referring to FIGS. 3 and 4, the AR object 94 includes a three-dimensional medical image associated with the head of the subject 91. The AR object 94 further includes a virtual first calibration rod 941, a virtual second calibration rod 942 and a virtual third calibration rod 943 respectively resembling the first calibration rod 62, the second calibration rod 63 and the third calibration rod 64. It is worth noting that dimensions of the virtual first calibration rod 941, the virtual second calibration rod 942 and the virtual third calibration rod 943 should respectively match the first calibration rod 62, the second calibration rod 63 and the third calibration rod 64 of the positioning frame 6.

In a calibration procedure, the virtual first calibration rod 941, the virtual second calibration rod 942 and the virtual third calibration rod 943 are respectively aligned with the first calibration rod 62, the second calibration rod 63 and the third calibration rod 64 of the positioning frame 6 so that the three-dimensional medical image is displayed at a corresponding position of the head of the subject 91.

In one embodiment, the head-mounted device 4 further includes an input unit (not shown) that is configured to be operated by the operator wearing the display device 4 to input data or commands. The input unit may be implemented by a touchpad, a button set, or a gesture controlled user interface, but implementation thereof is not limited to the disclosure herein and may vary in other embodiments.

In one embodiment, by moving in space or controlling the display device 4 to scale up/down or rotate the virtual first and second calibration rods 941 and 942 (as well as the AR object 94), the alignment of the first and second calibration rods 62 and 63 of the positioning frame 6 with the virtual first and second calibration rods 941 and 942 is initially performed. After the alignment is completed, parameters associated with relative position between the imaging capturing device 1, the display device 4 and the subject 91 are stored by the display device 4, and the relative position of the operator wearing the display device 4 with respect to the subject 91 is expected not to change. Afterward, the alignment of the third calibration rod 64 of the positioning frame 6 with the virtual third calibration rod 943 is performed. The calibration procedure can be repeated until the alignment of the first, second and third calibration rods 62 to 64 of the positioning frame 6 with the virtual first, second and third calibration rods 941 to 943 is satisfactory. After the alignment of the third calibration rod 64 of the positioning frame 6 with the virtual third calibration rods 943 is confirmed by the operator through the input unit, the parameters associated with the relative positions of the first, second and third calibration rods 62 to 64 of the positioning frame 6 and the virtual first, second and third calibration rods 941 to 943 are stored by the display device 4 or transmitted by the display device 4 to the processor 5.

In this embodiment, the three-dimensional medical image of the AR object 94 includes one of a magnetic resonance imaging (MRI) image, a computed tomography (CT) image, a two-dimensional cross sectional medical ultrasound image, and a three-dimensional model reconstructed from medical ultrasound images. However, implementation of the three-dimensional medical image of the AR object 94 is not limited to the disclosure herein and may vary in other embodiments. It should be noted that the three-dimensional model may be reconstructed by the processor 5 or by another computing device based on multiple two-dimensional medical images regarding, e.g., skin, brain or bone of the subject 91 so as to provide information of a spatial structure of, e.g., the skin, brain or bone of the subject 91. Since implementation of the generation of the three-dimensional model is well known in the art, detailed explanation of the same is omitted herein for the sake of brevity.

It should be noted that implementation of the calibration procedure is not limited to the disclosure herein. For example, in one embodiment, the AR object 94 includes a plurality of virtual facial features resembling facial features (e.g., eyes or ears) of the subject 91 and a three-dimensional medical image associated with the head of the subject 91. In a calibration procedure of this embodiment, the virtual facial features of the AR object 94 are aligned with the facial features of the subject 91 so that the three-dimensional medical image is displayed at a corresponding position of the head of the subject 91.

Figure 5:
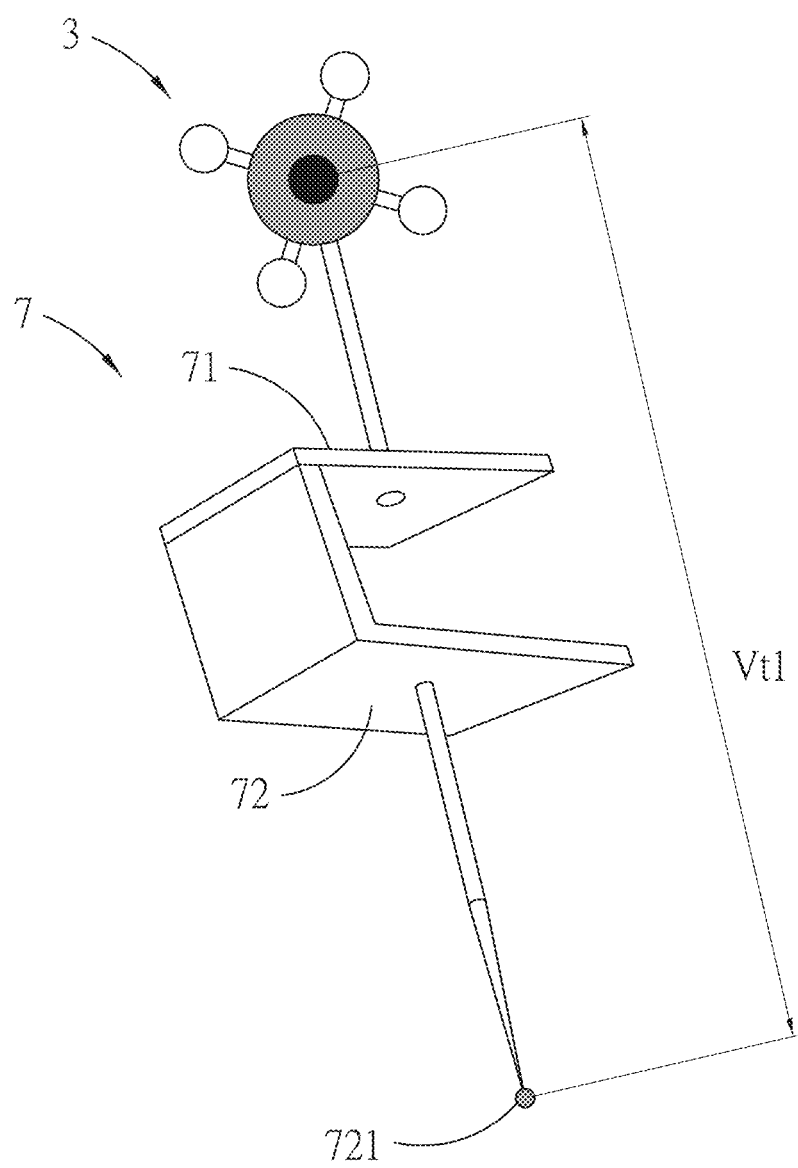
FIG. 5 is a schematic diagram illustrating an embodiment of a calibration tool of the system according to the disclosure.

Referring to FIGS. 1, 5, 6 and 7, in one embodiment, the treatment tool 92 is implemented to be an ultrasonic probe 95, and the tip 93 of the treatment tool 92 is a focal point 951 of ultrasound energy emitted by the ultrasonic probe 95. In this embodiment, the system further includes a calibration tool 7 that is configured to be utilized in combination with the ultrasonic probe 95. The calibration tool 7 includes an upper part 71 and a lower part 72 that has an end point 721 as shown in FIG. 5. The lower part 72 of the calibration tool 7 is configured to be separable from the upper part 71 of the calibration tool 7 such that the upper part 71 remains combined with the ultrasonic probe 95 when the lower part 72 is separated from the upper part 71 as shown in FIG. 7.

Figure 6:
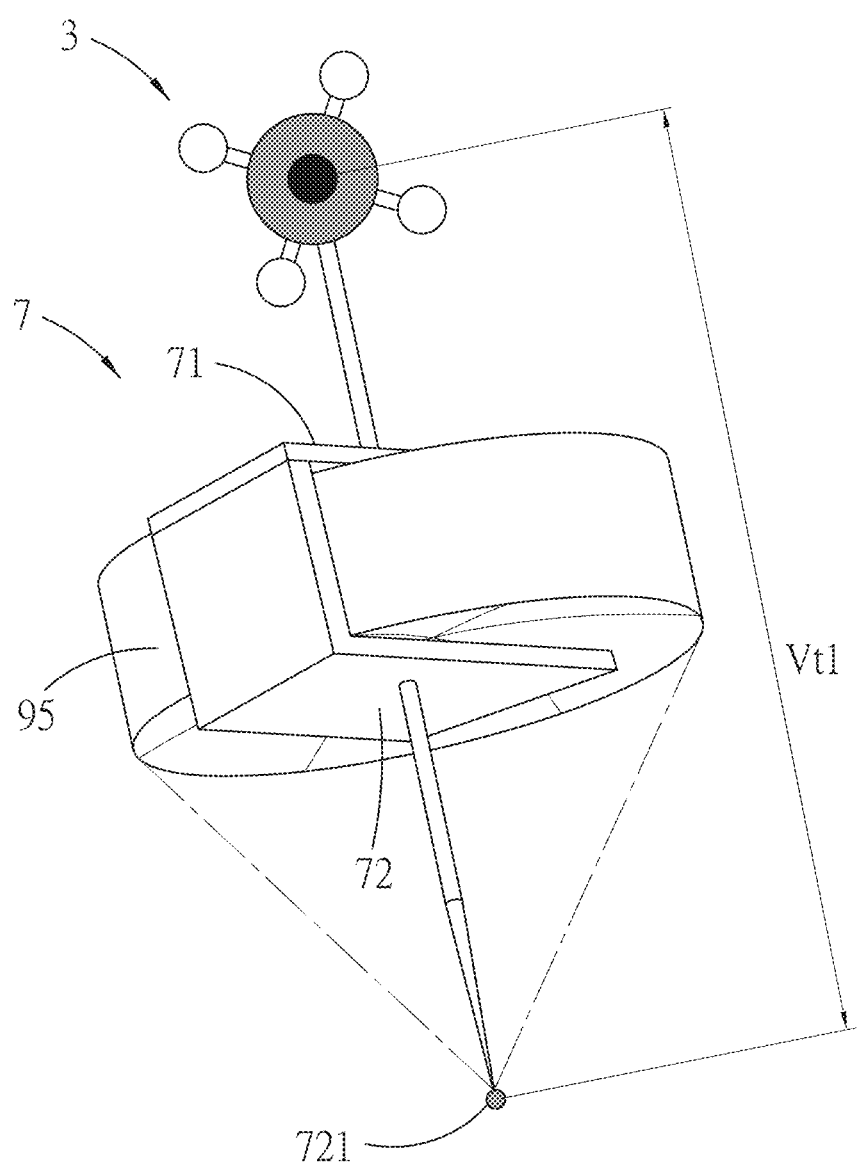
FIGS. 6 and 7 are schematic diagrams illustrating an embodiment of an ultrasound probe and the calibration tool of the system according to the disclosure.

The tool reference marker 3 is disposed on the upper part 71 of the calibration tool 7. As shown in FIG. 6, when the calibration tool 7 is combined with the ultrasonic probe 95, a distance (Vt1) between the tool reference marker 3 and the end point 721 of the lower part 72 of calibration tool 7 is equal to a distance (Vt1') between the tool reference marker 3 and the focal point 951 after the calibration procedure has been executed by the system with respect to the ultrasonic probe 95 as shown in FIG. 7. Since the distance (Vt1) between the tool reference marker 3 and the end point 721 of the lower part 72 of calibration tool 7 is predetermined, the second spatial transformation matrix T2 is able to be determined by the processor 5 through performing spatial analysis on images of the tool reference marker 3 captured by the image capturing device 1. Consequently, a corresponding position of the focal point 951, which is invisible in real space, can be determined so as to enable the display device 4 to correctly display a virtual focal point through the see-through display 42.

In other embodiments, the system according to the disclosure may be implemented to perform the calibration procedure with respect to treatment tools which emit invisible energy for medical treatment, such as focused ultrasound treatment, microwave treatment, light amplification by the stimulated emission of radiation (LASER) treatment, electromagnetic stimulation, and radio-frequency (RF) electromagnetic treatment.

Referring to FIG. 8, a second embodiment of the system for facilitating medical treatment is illustrated. The system is adapted to be utilized by an operator group 90 to perform an operation on a subject 91 with assistance of a treatment tool 92. The system includes an image capturing device 1, a first inertial sensor 82 that is disposed on the image capturing device 1, a tool reference marker 3 that is disposed on the treatment tool 92, a second inertial sensor 83 that is disposed on the tool reference marker 3, a display device 4, and a processor 5 that is electrically connected to the image capturing device 1, the first inertial sensor 82, the second inertial sensor 83 and the display device 4.

The image capturing device 1, along with the first inertial sensor 82, is disposed on the display device 4. The image capturing device 1 is configured to capture an image of the treatment tool 92. It should be noted that the image capturing device 1 merely includes one image capturing module which may be implemented by a camera or a video recorder.

The first inertial sensor 82 is configured to make inertial measurement of the image capturing device 1 and to generate a first orientation vector $\phi_t$ based on a result of the inertial measurement of the image capturing device 1. The second inertial sensor 83 is configured to make inertial measurement of the tool reference marker 3 and to generate a second orientation vector $\phi_r$ based on a result of the inertial measurement of the tool reference marker 3. Each of the first inertial sensor 82 and the second inertial sensor 83 may be implemented to be a three-axis accelerometer, a six-axis accelerometer, or any circuit configurable/programmable in a software manner and/or hardware manner to implement functionalities of an accelerometer or a magnetometer. In this embodiment, each of the first orientation vector $\phi_t$ and the second orientation vector $\phi_r$ is implemented to be an Euler angle, but implementation thereof is not limited to the disclosure herein and may vary in other embodiments.

In this embodiment, the tool reference marker 3 is implemented to be a colored circle or a colored rectangle so that a shape of the tool reference marker 3 in images thereof captured by the image capturing device 1 can be easily recognized by the processor 5. However, implementation of the tool reference marker 3 is not limited to the disclosure herein and may vary in other embodiments.

Figure 10:
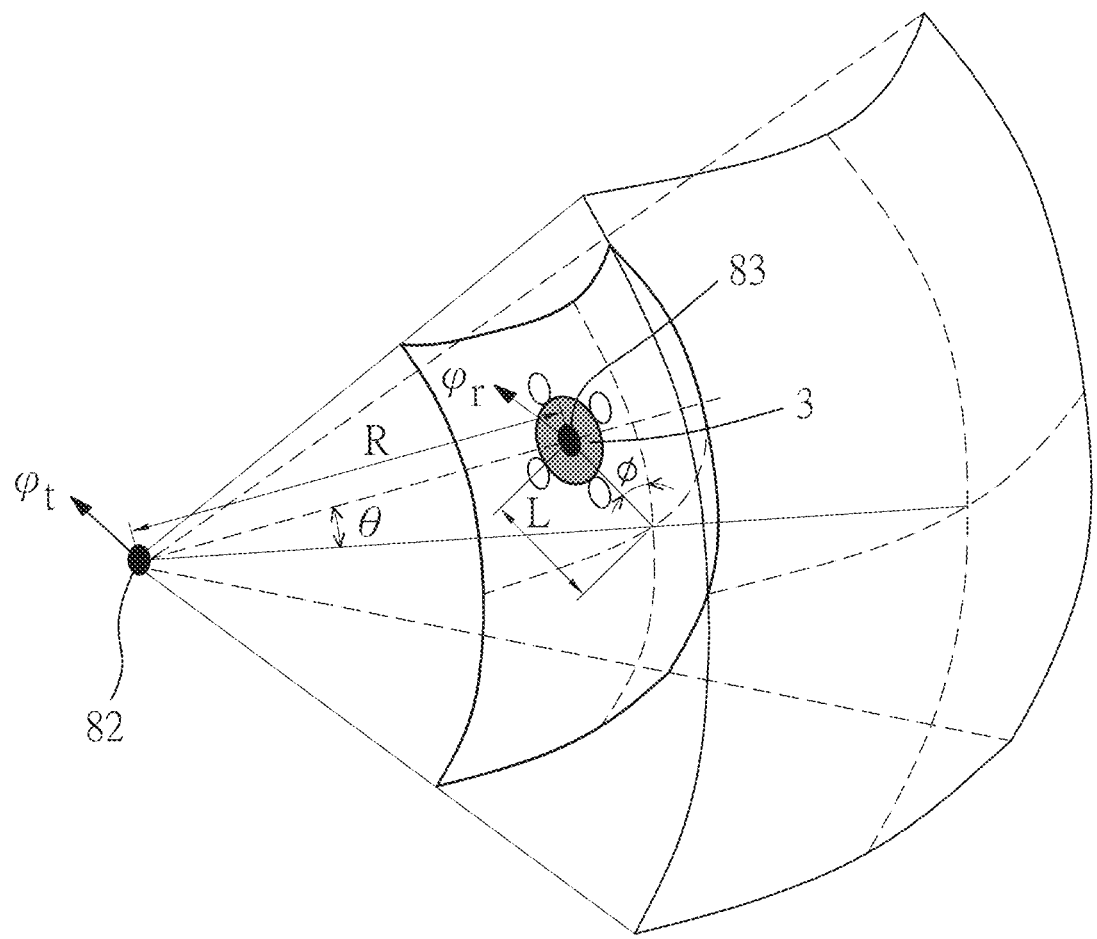
FIG. 10 is a schematic diagram illustrating an embodiment of capturing an image by the system according to the disclosure.
Figure 11:
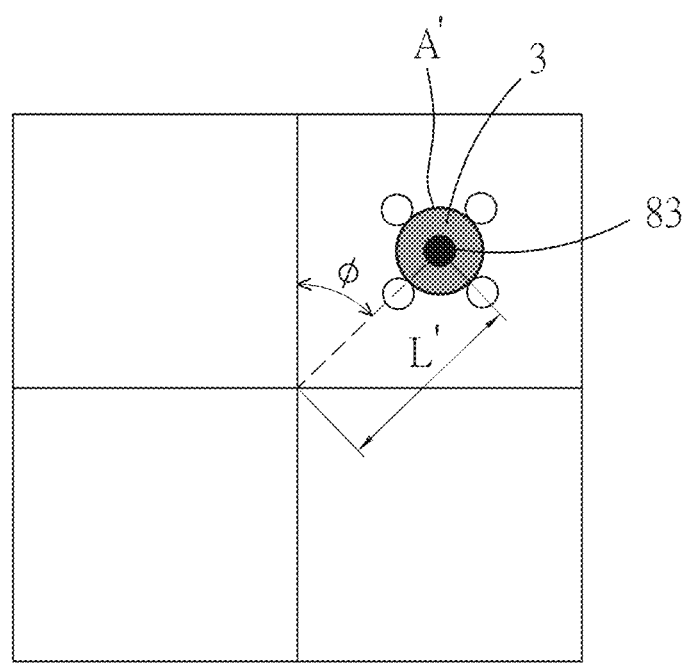
FIG. 11 is a schematic diagram of an embodiment of the image captured by the system.

The processor 5 is configured to receive the image, the first orientation vector $\phi_t$ and the second orientation vector $\phi_r$, and to calculate coordinates defining a spatial location of the tool reference marker 3 with respect to the image capturing device 1 based on the first orientation vector $\phi_t$, the second orientation vector $\phi_r$, an area A' of the tool reference marker 3 in the image, a position of the tool reference marker 3 in the image, and an actual distance R between the image capturing device 1 and the tool reference marker 3 (see FIGS. 10 and 11).

In this embodiment, the processor 5 is electrically connected to and communicable with the image capturing device 1 by means of wireless communication. The processor 5 may be implemented by a Central Processing Unit (CPU) in a computer, a microprocessor or any circuit configurable or programmable in a software manner and/or hardware manner to implement functionalities mentioned in this disclosure. However, implementation of the processor 5 is not limited to the disclosure herein.

FIG. 10 illustrates that the image capturing device 1 (see FIG. 8) is capturing an image of the tool reference marker 3, where the tool reference marker 3 is positioned on an imaginary curved plane which represents a plane of focus (POF) of the image capturing device 1. FIG. 11 is a schematic diagram illustrating the image of the tool reference marker 3 captured by the image capturing device 1. The processor 5 performs the following steps S1 to S8 to obtain coordinates (x,y,z) defining the spatial location of the tool reference marker 3 with respect to the image capturing device 1.

In step S1, the processor 5 calculates the area A' of the tool reference marker 3 in the image as shown in FIG. 11 by pixel-counting.

In step S2, the processor 5 receives the first orientation vector $\phi_t$ and the second orientation vector $\phi_r$ respectively from the first inertial sensor 82 and the second inertial sensor 83. It is worth noting that the first orientation vector $\phi_t$ represents an Euler angle of the image capturing device 1, and the second orientation vector $\phi_r$ represents an Euler angle of the second inertial sensor 83.

In step S3, the image capturing device 1 and the tool reference marker 3 are arranged in advance, i.e., the display device 4 and the treatment tool 92 are arranged in advance, such that the first orientation vector $\phi_t$ outputted by the first inertial sensor 82 disposed on the image capturing device 1 is equal to the second orientation vector $\phi_r$ outputted by the second inertial sensor 83 disposed on the tool reference marker 3. It should be noted that in other embodiments, the first orientation vector $\phi_t$ and the second orientation vector $\phi_r$ may not be adjusted in advance to be equal to each other, but may be adjusted later based on a predetermined mathematical relationship (i.e., the relative positions of the display device 4 and the treatment tool 92 are fixed).

In step S4, the processor 5 calculates an estimated actual area A of the tool reference marker 3 based on a mathematical relationship A=A'·arg($\phi_t$), where arg($\phi_t$) is equal to the argument of the first orientation vector $\phi_t$ when the first orientation vector $\phi_t$ is represented as a complex number.

In step S5, based on the first orientation vector $\phi_t$, the second orientation vector $\phi_r$, the area A' of the tool reference marker 3 in the image, and the position of the tool reference marker 3 in the image, the processor 5 calculates the actual distance R between the tool reference marker 3 and the image capturing device 1 as shown in FIGS. 8 and 10 by means of geometric relationships. It should be noted that the actual distance R between the tool reference marker 3 and the image capturing device 1 is substantially equal to a distance between the first inertia sensor 82 and the second inertia sensor 83. In this embodiment, the processor 5 calculates the actual distance R between the tool reference marker 3 and the image capturing device 1 according to a mathematical relationship:

$$\frac{R_{cal}}{R_{cal}-R} = \frac{\sqrt{A_{cal}}}{\sqrt{A_{cal}}-\sqrt{A}},$$

where $R_{cal}$ is a predetermined distance, $A_{cal}$ is an area of the tool reference marker 3 calculated when the tool reference marker 3 is spaced apart from the image capturing device 1 by the predetermined distance $R_{cal}$, A is the estimated actual area of the tool reference marker 3 calculated by the processor 5 in step S4 based on the first orientation vector $\phi_t$, the second orientation vector $\phi_r$, and the area A' of the tool reference marker 3 in the image.

In step S6, referring to FIGS. 10 and 11, based on the position of the tool reference marker 3 in the image, the processor 5 calculates an actual distance L between the tool reference marker 3 and an optical axis of the image capturing device 1. Specifically speaking, the processor 5 determines the position of the tool reference marker 3 in the image represented as (L',$\phi$), where $\phi$ is an angle formed by a vertical axis passing through a center of the image and an imaginary line connecting the center of the image and the tool reference marker 3, and L' is a length of the imaginary line connecting the center of the image and the tool reference marker 3 in the image. The angle φ in the image shown in FIG. 11 and an actual corresponding angle (also denoted by φ) shown in FIG. 10 are equal to each other. The processor 5 then calculates the actual distance L between the tool reference marker 3 and an optical axis of the image capturing device 1 based on the length L' and a ratio between the area A' of the tool reference marker 3 in the image and the estimated actual area A of the tool reference marker 3.

In step S7, based on the actual distance R between the tool reference marker 3 and the image capturing device 1 and the actual distance L between the tool reference marker 3 and the optical axis of the image capturing device 1, the processor 5 calculates an angle of the tool reference marker 3 with respect to the optical axis of the image capturing device 1 as shown in FIG. 10 by a mathematical relationship:

$$\theta = \arcsin\left(\frac{L}{R}\right).$$

In step S8, the processor 5 further calculates the coordinates (x,y,z) defining the spatial location of the tool reference marker 3 with respect to the image capturing device 1 according to:

$$x = R \cdot \sin\theta \cdot \sin\phi,$$
$$y = R \cdot \sin\theta \cdot \cos\phi,$$
$$z = R \cdot \cos\phi,$$
$$\text{where } \theta = \arcsin\left(\frac{L}{R}\right),$$

and φ is the angle formed by the vertical axis passing through the center of the image and the imaginary line connecting the center of the image and the tool reference marker 3 in the image.

Figure 9:
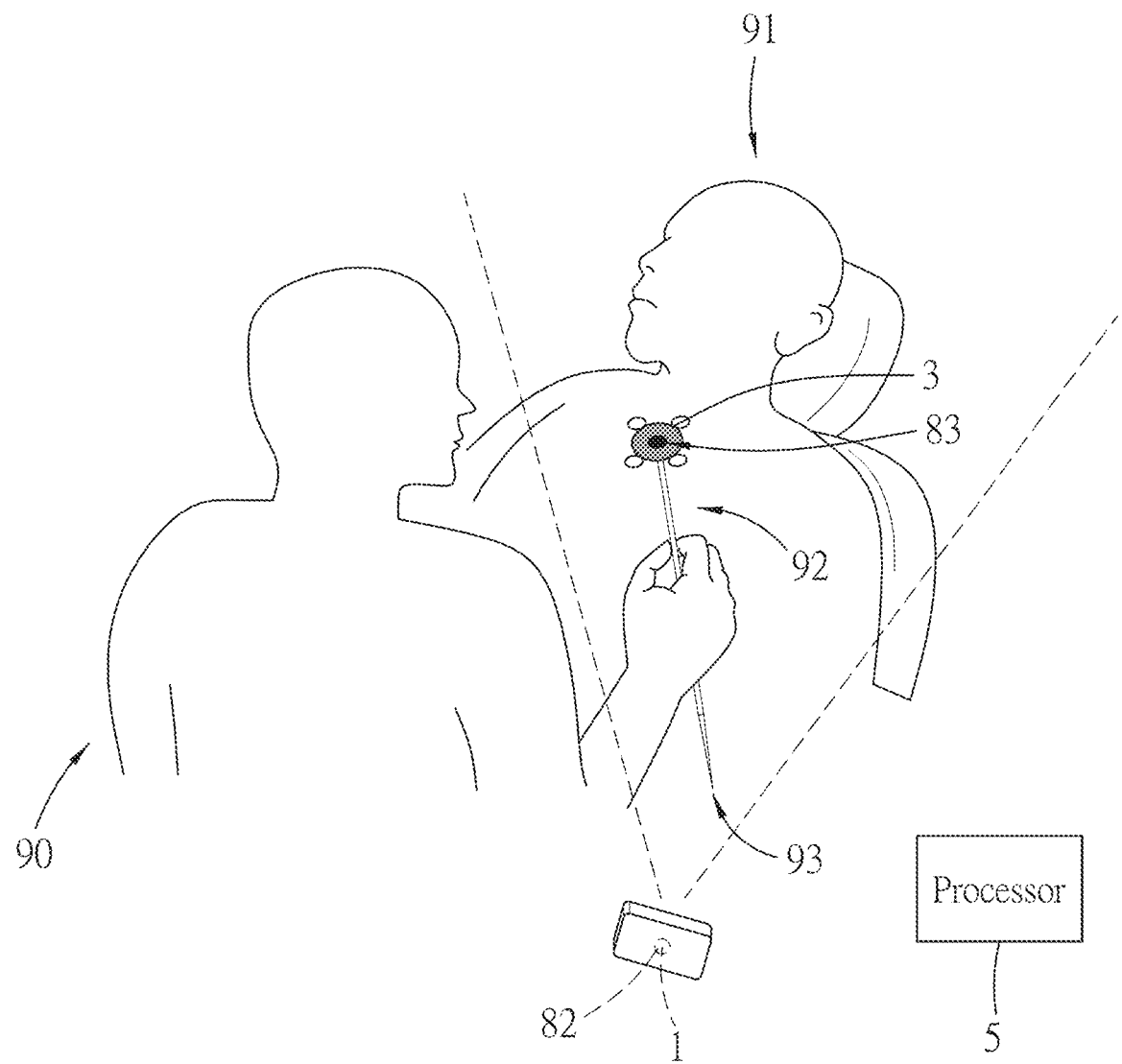
FIG. 9 is a schematic diagram illustrating a third embodiment of the system for facilitating medical treatment according to the disclosure.

Referring to FIG. 9, a third embodiment of the system for facilitating medical treatment is illustrated. The third embodiment is similar to the second embodiment, but is different from the second embodiment in aspects described as follows. The image capturing device 1 and the first inertia sensor 82 disposed thereon are not disposed on the display device 4 worn by the operator, but instead are positioned near the subject 91 (i.e., the patient). Similar to the second embodiment of the system, the processor 5 calculates the coordinates (x,y,z) defining the spatial location of the tool reference marker 3, which may represent the spatial location of the second inertia sensor 83 as well, with respect to the image capturing device 1 as an origin. Thereafter, similar to the first embodiment of the system according to the disclosure, the processor 5 controls the see-through display 42 of the display device 4 (see FIG. 1) or a conventional computer display (not shown) to display the auxiliary information at the desired position based on the coordinates (x,y,z) thus calculated.

It should be noted that in the second and third embodiments of the system according to the disclosure, the coordinates (x,y,z) defining the spatial location of the tool reference marker 3 (or the second inertia sensor 83) correspond to the second vector matrix X2 calculated in the first embodiment of the system according to the disclosure. Therefore, coordinate information regarding a spatial location of a tip 93 of the treatment tool 92 in the second or third embodiment of the system may be calculated similarly to the way of calculating the third vector matrix X3 described in the first embodiment of the disclosure. Additionally, the way of calculating the coordinates (x,y,z) defining the spatial location of the tool reference marker 3 in the second and third embodiments may be utilized in the first embodiment of the system to calculate the second vector matrix X2.

Figure 12:
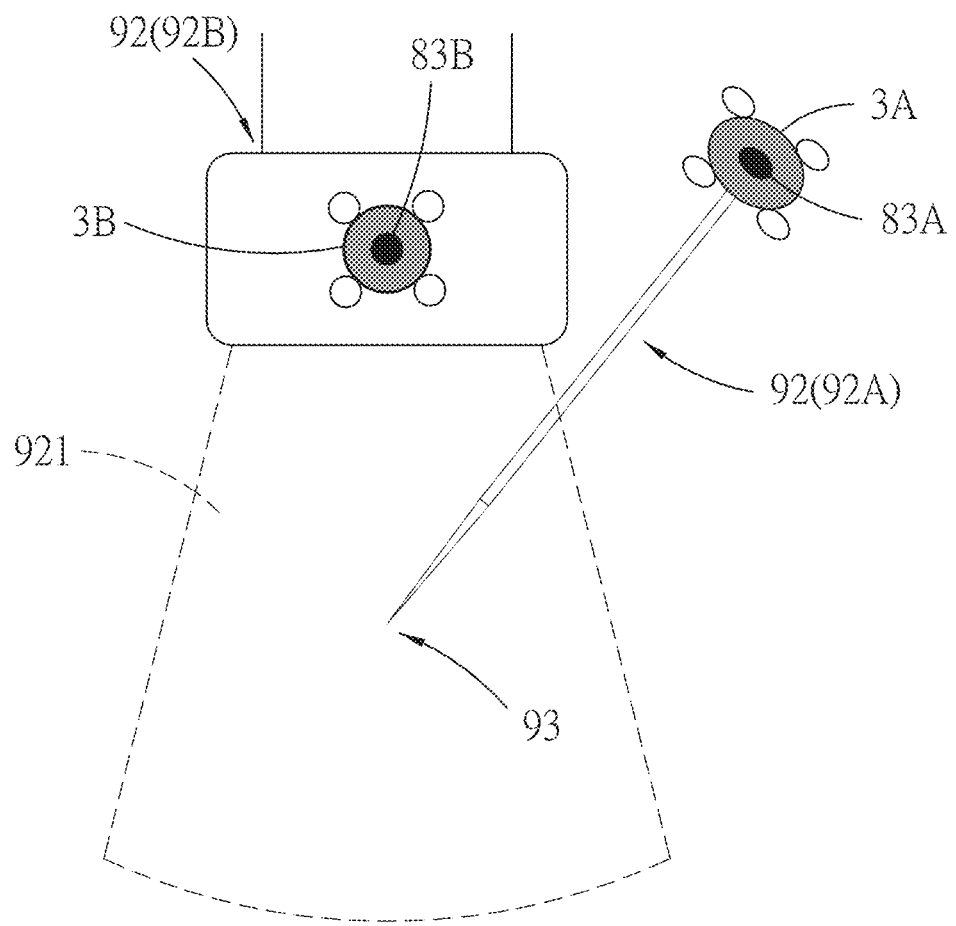
FIG. 12 is a schematic diagram of embodiments of treatment tools.

In one embodiment as shown in FIG. 12, there are two treatment tools 92, one of which is implemented to be a surgical instrument (92A), and the other one of which is implemented to be a handheld tool (92B) for diagnosis by means of ultrasound. Two tool reference markers (3A) and (3B) are respectively disposed on the surgical instrument (92A) and the handheld tool (92B), and two second inertia sensors (83A) and (83B) are respectively disposed on the surgical instrument (92A) and the handheld tool (92B) as well. Ultrasound energy emitted by the handheld tool (92B) defines a treatment field 921 that is a spatial region in which the emitted ultrasound energy is effective for treatment. The system of this disclosure is capable of tracking spatial positions of the treatment field 921 and a tip 93 of the surgical instrument (92A) based on results of measurement by the second inertia sensors (83A) and (83B) and based on calculations of the first vector matrix X1, the second vector matrix X2 and the third vector matrix X3. The processor 5 (see FIG. 1) is configured to enable the display device 4 (see FIG. 1) to correctly display virtual images of the treatment field 921 with respect to the tip 93 of the surgical instrument (92A) through the see-through display 42 (see FIG. 1).

In summary, the system for facilitating medical treatment according to the disclosure captures images of the reference markers on the operator, the subject and the treatment tool, and analyzes the images to obtain spatial locations of the reference markers. Thereafter, the system provides the auxiliary information regarding the subject based on the coordinate information regarding the spatial locations, so as to facilitate performance of medical treatment with the treatment tool by the operator wearing the display device. Specifically speaking, the system enables the operator to see the subject and the AR object regarding the subject at the same time. In addition, medical images regarding the subject can be displayed at the desired position with respect to the subject because of the coordinate information thus calculated. Furthermore, important information in the medical images can be displayed through the see-through display by means of AR so as to assist the operator in operating the treatment tool for performing the medical treatment on the subject and making medical decision in time.

In the description above, for the purposes of explanation, numerous specific details have been set forth in order to provide a thorough understanding of the embodiments. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects, and that one or more features or specific details from one embodiment may be practiced together with one or more features or specific details from another embodiment, where appropriate, in the practice of the disclosure.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. A system for facilitating medical treatment, adapted to be utilized by an operator group to perform an operation on a subject with assistance of a treatment tool, said system comprising:
   an image capturing device including two image capturing modules configured to simultaneously and respectively capture two images of the operator group, the subject and the treatment tool;
   a subject reference marker to be disposed adjacent to the subject;
   a tool reference marker to be disposed on the treatment tool;
   at least one display device configured to be mounted on one member of the operator group;
   at least one operator reference marker disposed on said at least one display device; and
   a processor that is electrically connected to said image capturing device, that is communicable with said at least one display device, and that is configured to receive the images, to perform a spatial analysis on the images so as to obtain spatial locations of said subject reference marker, said tool reference marker and said at least one operator reference marker, and to transmit auxiliary information regarding the subject and coordinate information regarding the spatial locations to said at least one display device,
   wherein the auxiliary information contains an augmented reality (AR) object related to treatment of the subject, and said at least one display device is a head-mounted device including a see-through display that is configured to display the AR object at a desired position with respect to one of the subject and the treatment tool based on the auxiliary information and the coordinate information regarding the spatial locations;
   wherein said at least one operator reference marker and said at least one display device are both plural in number; and
   wherein said processor is configured to calculate coordinate vectors $V=(O, V_1, V_2, \ldots, V_N, V_t, V_f)$ based on the spatial locations of said subject reference marker, said tool reference marker and said operator reference markers that are each defined in a form of coordinates in a coordinate system, where O represents coordinates of an origin of the coordinate system and corresponds to a spatial location of said image capturing device, N represents a total number of said operator reference markers, $V_i$ represents a vector from the origin to coordinates of the $i^{th}$ one of said operator reference markers, where i is an integer from one to N, $V_t$ represents a vector from the origin to coordinates of said tool reference marker, and $V_f$ represents a vector from the origin to coordinates of said subject reference marker.

2. The system as claimed in claim 1, wherein said processor is configured to, based on the coordinate vectors, calculate a first vector matrix $$X1=(V_t-V_1, V_t-V_2, \ldots, V_t-V_N, V_f-V_t, V_1-V_f, V_2-V_f, \ldots, V_N-V_f)$$

that serves as the coordinate information, in which the spatial location of said image capturing device (1) serves as the origin of the coordinate system.

3. The system as claimed in claim 1, wherein said processor is configured to, based on the coordinate vectors and a predetermined first spatial transformation matrix, calculate a second vector matrix $$X2=T1*(V_t-V_1, V_t-V_2, \ldots, V_t-V_N, V_f-V_t, V_1-V_f, V_2-V_f, \ldots, V_N-V_f)$$

that serves as the coordinate information, in which the spatial locations of said operator reference markers respectively serve as origins of respective coordinate systems, so said head-mounted devices obtain plural sets of real-time coordinates of said tool reference marker, each with respect to a respective one of said operator reference markers.

4. The system as claimed in claim 1, wherein said processor is configured to, based on the coordinate vectors V, a predetermined first spatial transformation matrix T1 and a predetermined second spatial transformation matrix T2, calculate a third vector matrix $$X3=T2*T1*(V_t-V_1, V_t-V_2, \ldots, V_1-V_N, V_f-V_t, V_1-V_f, V_2-V_f, \ldots, V_N-V_f)$$

that serves as the coordinate information, in which the spatial locations of said operator reference markers respectively serve as origins of respective coordinate systems, so said head-mounted devices obtain plural sets of real-time coordinates of a tip of the treatment tool, each with respect to a respective one of said operator reference markers.

5. The system as claimed in claim 4, the treatment tool being an ultrasonic probe, and the tip of the treatment tool being a focal point of ultrasound energy emitted by the ultrasonic probe, said system further comprising:
   a calibration tool configured to be utilized in combination with the ultrasonic probe, and including an upper part and a lower part that has an end point,
   wherein said tool reference marker is disposed on said upper part of said calibration tool, a distance between said tool reference marker and said end point of said lower part of calibration tool being equal to a distance between said tool reference marker and the focal point when said calibration tool is combined with the ultrasonic probe, and
   said lower part of said calibration tool is configured to be separable from said upper part of said calibration tool such that said upper part remains combined with the ultrasonic probe when said lower part is separated from said upper part.

6. The system as claimed in claim 1, wherein the AR object includes a plurality of virtual facial features resembling facial features of the subject and a three-dimensional medical image associated with the head of the subject,
   in a calibration procedure, the virtual facial features of the AR object being aligned with the facial features of the subject so that the three-dimensional medical image is displayed at a corresponding position of the head of the subject.

7. The system as claimed in claim 1, further comprising:
   a positioning frame including
      a frame body that is configured to be worn on a head of the subject, a first calibration rod, a second calibration rod and a third calibration rod that are disposed on said frame body, wherein:

said first calibration rod and said second calibration rod are configured to be arranged along an imaginary axis so that, when said frame body is worn on the head of the subject, said first calibration rod and said second calibration rod respectively abut against two ears of the subject, said third calibration rod (64) is configured to be arranged to abut against a lower jaw of the subject (91), the AR object includes a three-dimensional medical image associated with the head of the subject, and a virtual first calibration rod, a virtual second calibration rod and a virtual third calibration rod respectively resembling said first calibration rod, said second calibration rod and said third calibration rod, and in a calibration procedure, the virtual first calibration rod, the virtual second calibration rod and the virtual third calibration rod are respectively aligned with said first calibration rod, said second calibration rod and said third calibration rod so that the three-dimensional medical image is displayed at a corresponding position of the head of the subject.

8. The system as claimed in claim 7, wherein the three-dimensional medical image of the AR object includes one of a magnetic resonance imaging (MRI) image, a computed tomography (CT) image, a two-dimensional cross sectional medical ultrasound image, and a three-dimensional model reconstructed from medical ultrasound images.

9. A system for facilitating medical treatment, adapted to be utilized by an operator group to perform an operation on a subject with assistance of a treatment tool, said system comprising:

an image capturing device configured to capture an image of the treatment tool;

a first inertial sensor disposed on said image capturing device, and configured to make inertial measurement of said image capturing device and to generate a first orientation vector based on a result of the inertial measurement of said image capturing device;

a tool reference marker to be disposed on the treatment tool;

a second inertial sensor disposed on said tool reference marker, and configured to make inertial measurement of said tool reference marker and to generate a second orientation vector based on a result of the inertial measurement of said tool reference marker; and a processor that is electrically connected to said image capturing device, said first inertial sensor and said second inertial sensor, and that is configured to receive the image, the first orientation vector and the second orientation vector, and to calculate coordinates defining a spatial location of said tool reference marker with respect to said image capturing device based on the first orientation vector, the second orientation vector, an area of said tool reference marker in the image, and a position of said tool reference marker in the image, wherein said processor is configured to, based on the first orientation vector, the second orientation vector, the area of said tool reference marker in the image, and the position of said tool reference marker in the image, calculate an actual distance between said tool reference marker and said image capturing device and an actual distance between said tool reference marker and an optical axis of said image capturing device, said processor further configured to calculate the coordinates (x, y, z) defining the spatial location of said tool reference marker with respect to said image capturing device according to:

$$x = R \cdot \sin\theta \cdot \sin\phi,$$
$$y = R \cdot \sin\theta \cdot \cos\phi,$$
$$z = R \cdot \cos\phi,$$
$$\text{where } \theta = \arcsin\left(\frac{L}{R}\right),$$

R denotes the actual distance between said tool reference marker and said image capturing device, L denotes the actual distance between said tool reference marker and the optical axis of said image capturing device, and $\phi$ is an angle formed by a vertical axis passing through a center of the image and an imaginary line connecting the center of the image and said tool reference marker in the image.

10. The system as claimed in claim 9, wherein said processor is configured to calculate the actual distance between said tool reference marker and said image capturing device according to a mathematical relationship:

$$\frac{R_{cal}}{R_{cal} - R} = \frac{\sqrt{A_{cal}}}{\sqrt{A_{cal}} - \sqrt{A}},$$

where R denotes the actual distance between said tool reference marker and said image capturing device, $R_{cal}$ is a predetermined distance, $A_{cal}$ is an area of said tool reference marker calculated when said tool reference marker is spaced apart from said image capturing device by the predetermined distance $R_{cal}$, A is an estimated actual area of said tool reference marker calculated by said processor based on the first orientation vector, the second orientation vector, and the area of said tool reference marker in the image.

11. The system as claimed in claim 10, wherein:

said image capturing device and said tool reference marker are arranged such that the first orientation vector is equal to the second orientation vector; and said processor is configured to calculate the estimated actual area of said tool reference marker based on a mathematical relationship $A = A' \cdot \arg(\phi_t)$ where A denotes the estimated actual area of said tool reference marker and $\phi_t$ denotes the first orientation vector.

12. A system for facilitating medical treatment, adapted to be utilized by an operator group to perform an operation on a subject with assistance of a treatment tool, said system comprising:

an image capturing device including two image capturing modules configured to simultaneously and respectively capture two images of the operator group, the subject and the treatment tool;

a subject reference marker to be disposed adjacent to the subject;

a tool reference marker to be disposed on the treatment tool;

at least one display device configured to be mounted on one member of the operator group;

at least one operator reference marker disposed on said at least one display device; and a processor that is electrically connected to said image capturing device, that is communicable with said at least one display device, and that is configured to receive the images, to perform a spatial analysis on the images so as to obtain spatial locations of said subject reference marker, said tool reference marker and said at least one operator reference marker, and to transmit auxiliary information regarding the subject and coordinate information regarding the spatial locations to said at least one display device, wherein the auxiliary information contains an augmented reality (AR) object related to treatment of the subject, and said at least one display device is a head-mounted device including a see-through display that is configured to display the AR object at a desired position with respect to one of the subject and the treatment tool based on the auxiliary information and the coordinate information regarding the spatial locations;

said system further comprising:
a positioning frame including
a frame body that is configured to be worn on a head of the subject,
a first calibration rod, a second calibration rod and a third calibration rod that are disposed on said frame body, wherein:

said first calibration rod and said second calibration rod are configured to be arranged along an imaginary axis so that, when said frame body is worn on the head of the subject, said first calibration rod and said second calibration rod respectively abut against two ears of the subject, said third calibration rod is configured to be arranged to abut against a lower jaw of the subject, the AR object includes a three-dimensional medical image associated with the head of the subject, and a virtual first calibration rod, a virtual second calibration rod and a virtual third calibration rod respectively resembling said first calibration rod, said second calibration rod and said third calibration rod, and in a calibration procedure, the virtual first calibration rod, the virtual second calibration rod and the virtual third calibration rod are respectively aligned with said first calibration rod, said second calibration rod and said third calibration rod so that the three-dimensional medical image is displayed at a corresponding position of the head of the subject.

\* \* \* \* \*